US00PP24524P3

(12) United States Plant Patent
Korlipara

(10) Patent No.: US PP24,524 P3
(45) Date of Patent: Jun. 3, 2014

(54) *ECHINACEA* PLANT NAMED 'COLORBURST ORANGE'

(50) Latin Name: ***Echinacea* hybrid**
Varietal Denomination: Colorburst Orange

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 101 days.

(21) Appl. No.: 13/573,326

(22) Filed: Sep. 11, 2012

(65) Prior Publication Data

US 2014/0075629 P1 Mar. 13, 2014

(51) Int. Cl.
*A01H 5/00* (2006.01)

(52) U.S. Cl.
USPC ..... Plt./428; Plt./263.1

(58) Field of Classification Search
USPC ..... Plt./263.1, 428
See application file for complete search history.

*Primary Examiner* — Susan McCormick Ewoldt
(74) *Attorney, Agent, or Firm* — Klarquist Sparkman, LLP

(57) ABSTRACT

A new and distinct *Echinacea* plant named 'Colorburst Orange' characterized by clear orange ray and disc florets, very long disc florets forming an frilly double "anemone"-type inflorescence, very lobed ray florets making a frilly appearance, a medium short size and with excellent stem count and branching, and excellent vigor.

1 Drawing Sheet

Botanical denomination: *Echinacea* hybrid.
Variety designation: 'Colorburst Orange'.

BACKGROUND OF THE INVENTION

The present invention relates to a new and distinct cultivar of *Echinacea* and given the cultivar name 'Colorburst Orange'. *Echinacea* is in the family Asteraceae. The new cultivar is part of a planned breeding program for a series with compact habits and double "anemone"-type inflorescences. The exact parents of this selection are unknown, unnamed, proprietary interspecific hybrids of *Echinacea paradoxa*× *Echinacea purpurea*. The new cultivar stood out among the seedlings for its very long disc florets.

Compared to *Echinacea* 'Supreme Cantaloupe', U.S. Plant patent application Ser. No. 13/573,979, the new cultivar is taller and has longer, frillier disc florets and a more mounding habit.

Compared to *Echinacea* 'Marmalade' (U.S. Plant Pat. No. 22,602) the new cultivar has inflorescences a different shade of orange, clear orange rather than yellow orange.

This new *Echinacea* cultivar is distinguished by:

1. clear orange ray and disc florets,
2. very long disc florets forming an frilly double "anemone"-type inflorescence,
3. very lobed ray florets making a frilly appearance,
4. a medium short size and with excellent stem count and branching, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old plant of *Echinacea* 'Colorburst Orange' growing in the trial bed in full sun in mid-July in Canby, Oreg.

DETAILED PLANT DESCRIPTION

The following is a detailed description of the new *Echinacea* cultivar based on observations of two-year-old specimens growing in the trial bed in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart,* $5^{th}$ edition.

Plant:

*Type.*—Herbaceous perennial.
*Hardiness.*—USDA Zones 4 to 9.
*Size.*—Grows to about 60 cm wide and 60 cm tall to top of inflorescences.
*Form.*—Basal clump, with about 20 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 3 inflorescences per stem.
*Size.*—To 56 cm tall to a terminal inflorescence and 8 mm wide at base.
*Internode length.*—2 cm to 10 cm.
*Surface texture.*—Strigose.
*Color.*—Yellow Green 146C.

Leaf (basal):

*Type.*—Simple.

*Shape.*—Ovate to lanceolate.

*Arrangement.*—Basal.

*Blade size.*—Grows to 15.5 cm long and 6.5 cm wide.

*Margins.*—Serrate.

*Apex.*—Acuminate.

*Base.*—Attenuate.

*Surface texture.*—Strigose on both sides.

*Venation.*—Pinnate, Yellow Green 145C on top and bottom side.

*Color.*—Topside Green 137A, bottom side closest to Yellow Green 147B.

*Petiole description.*—Grows to 17 cm long and 2 mm wide above the clasp, glabrous, Yellow Green 145C and tinted Greyed Purple 187A at the base.

Leaf (stem):

*Type.*—Simple.

*Shape.*—Lanceolate.

*Arrangement.*—Alternate.

*Blade size.*—Grows to 13 cm long and 4 cm wide.

*Margins.*—Serrate.

*Apex.*—Acuminate.

*Base.*—Attenuate.

*Surface texture.*—Strigose on both sides.

*Venation.*—Pinnate, with 3 main veins from the base, Yellow Green 145C on top and bottom side.

*Color.*—Topside Green 137A, bottom side closest to Yellow Green 147B.

*Petiole description.*—On all but upper leaves, clasping, grows to 7.5 cm long and 4 mm wide above the clasp, strigose, both sides Yellow Green 146D.

Inflorescence:

*Type.*—Composite on terminal stalked heads.

*Number of flowering stems from the ground.*—About 24.

*Flowering stem.*—Grows to 56 cm tall from the base of the plant to the terminal inflorescence and can grow to 13 cm long from the top stem leaf to the base of an inflorescence; branched with 1 to 3 inflorescences per stem; diameter growing to 7 mm wide near the inflorescence; strigose; Yellow Green 146C.

*Size.*—Grows to 9 cm wide and 5 cm deep as disc enlarges.

*Form.*—Ray florets held slightly reflexed, mature disc is rounded.

*Immature inflorescence.*—Grows to 3.5 cm wide and 2 cm deep, ray florets held at a 45 degree angle from the horizontal and rolled up so only the back color shows, Greyed Yellow 160B tinted Greyed Red 182C on bottom ⅔, disc color Yellow Green 148A.

*Ray florets.*—With 1 pistil and 4 stamen, about 15 in number, grow to 45 mm long and 9 mm to 30 mm wide, oblanceolate with the tip variously lobed (2 to 5 lobed, usually 3 lobed with lobes 6 mm to 27 mm long and 1.5 mm to 3 mm wide), tips acute, entire margins, base attenuate, glabrous on both sides; top side Orange 26B blending to Orange 26A at the base, bottom side closest to Red 36A; pistil 11 mm long, ovary 4 mm long, White NN155A on bottom ½ and Yellow Green 148C tinted Brown 200C on top ½, style 5 mm and Red 36D, stigma Greyed Red 182C, anthers 4 mm long, filaments threadlike 2 mm long Greyed White 159A, anthers 2 mm long, sterile, Grey Brown N199B.

*Disc.*—Flat becoming conic, growing to 30 mm deep and 75 mm wide with maturity, Orange Red 35C when disc florets are closed to Orange 26A when disc florets are open.

*Disc florets.*—To about 280 in number, each with 1 pistil and 4 stamen, grow to 27 mm long and 5 mm to 14 mm wide, each with one persistent, very stiff linear bract (10.5 mm long with 1 mm Greyed Purple 187A at the tip blending to 2 mm Orange Red 31B to 5 mm Yellow Green 145D to White 155A at base); corollas to 26 mm long and 5 mm to 14 mm wide, tubular at base (2 mm to 4 mm long and 1.5 mm wide, 146C) then obovate with tip 3 to 4 lobed (lobes variable, linear to lanceolate, to 2 mm to 18 mm long and 1 mm to 3.5 mm wide), margin entire, tips acute, base attenuate, glabrous on both sides, topside Orange 31B, bottom side Greyed Red 182C on top ⅔ blending to Yellow 11C; pistil 12 mm long, ovary 2.5 mm long, White NN155A, style 8 mm and Red 36D, stigma Greyed Red 182C, anthers 5 mm long, filaments threadlike 2 mm long Greyed White 159A, anthers 2 mm long, sterile, Grey Brown N199B.

*Phyllaries.*—In 4 leafy series, area grows to 32 mm wide and 10 mm deep, lobes lanceolate in shape, reflexed, grow to 7 mm long and 3 mm wide, both sides Yellow Green 147B, margins strigose, tip acute, strigose.

*Receptacle.*—Grows to 9 mm wide and 9 mm deep, White NN155B.

*Bloom period.*—July through October in Canby, Oreg.

*Fragrance.*—Slight.

*Lastingness.*—Each inflorescence lasts about two weeks in Canby, Oreg.

Seeds: None seen.

*Fertility.*—Poor.

Disease and pests: No pests or diseases have been observed on plants grown under commercial conditions in Canby, Oreg. No resistances are known.

I claim:

1. A new and distinct *Echinacea* plant as herein illustrated and described.

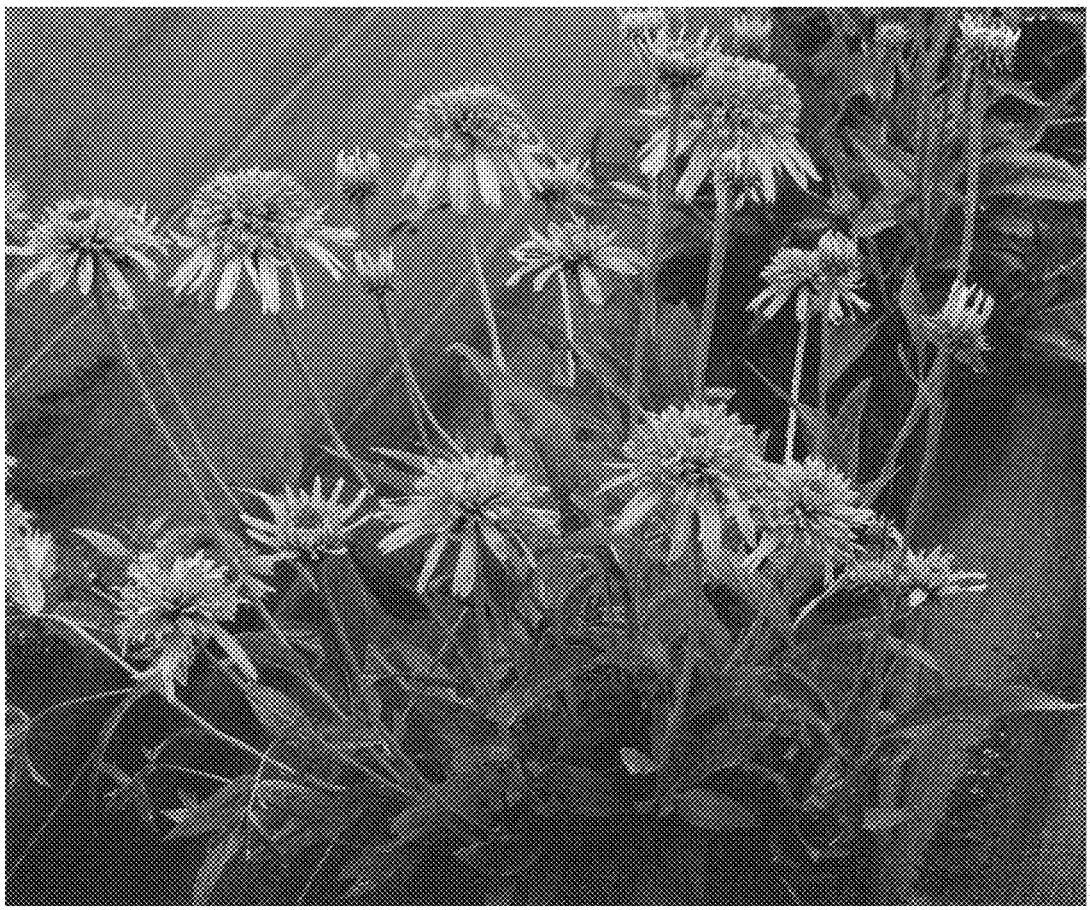

* * * * *